(12) United States Patent
Gaeta et al.

(10) Patent No.: US 9,662,317 B2
(45) Date of Patent: May 30, 2017

(54) METHODS OF ADMINISTERING TOLPERISONE FOR THERAPEUTIC PURPOSES

(71) Applicant: SANOCHEMIA PHARMAZEUTIKA AG, Vienna (AT)

(72) Inventors: Federico Gaeta, Mountain View, CA (US); Klaus Gerdes, Vienna (AT); Stefan Welzig, Vienna (AT); Beate Katz, Steinbrunn (AT); Jan Rothenburger, Oslip (AT); Jozsef Gungl, Sopron (HU)

(73) Assignee: SANOCHEMIA PHARMAZEUTIKA AG, Vienna (AT)

( * ) Notice: Subject to any disclaimer, the term of this patent is extended or adjusted under 35 U.S.C. 154(b) by 0 days.

(21) Appl. No.: 15/068,006

(22) Filed: Mar. 11, 2016

(65) Prior Publication Data

US 2016/0220549 A1 Aug. 4, 2016

Related U.S. Application Data

(62) Division of application No. 12/597,664, filed as application No. PCT/US2008/005281 on Apr. 24, 2008, now Pat. No. 9,315,480.

(60) Provisional application No. 61/023,799, filed on Jan. 25, 2008.

(30) Foreign Application Priority Data

Apr. 26, 2007 (AT) .................................. A 658/2007
Nov. 29, 2007 (AT) ................................. A 1953/2007

(51) Int. Cl.
| | | |
|---|---|---|
| C07D 211/20 | (2006.01) | |
| A61K 31/4453 | (2006.01) | |
| C07D 295/108 | (2006.01) | |
| A61K 9/00 | (2006.01) | |
| A61K 9/20 | (2006.01) | |

(52) U.S. Cl.
CPC ........ *A61K 31/4453* (2013.01); *A61K 9/0053* (2013.01); *A61K 9/20* (2013.01); *C07D 295/108* (2013.01); *Y10T 436/145555* (2015.01)

(58) Field of Classification Search
USPC ......................................................... 546/236
See application file for complete search history.

(56) References Cited

U.S. PATENT DOCUMENTS

| | | | |
|---|---|---|---|
| 4,814,179 A | 3/1989 | Bolton et al. | |
| 4,996,058 A | 2/1991 | Sinnreich | |
| 5,073,375 A | 12/1991 | Yoshida et al. | |
| 5,626,876 A | 5/1997 | Müller et al. | |
| 5,780,057 A | 7/1998 | Conte et al. | |
| 6,500,455 B1 | 12/2002 | Frantsits | |
| 6,861,072 B1 | 3/2005 | Alaux et al. | |
| 7,385,060 B2 | 6/2008 | Czollner et al. | |
| 8,372,979 B2 | 2/2013 | Welzig et al. | |
| 9,315,480 B2 | 4/2016 | Gaeta et al. | |
| 2005/0196451 A1 | 9/2005 | Bodenteich et al. | |
| 2006/0004050 A1 | 1/2006 | Speicher et al. | |
| 2006/0013876 A1 | 1/2006 | Lohray et al. | |
| 2006/0041141 A1 | 2/2006 | Czollner et al. | |
| 2006/0198888 A1 | 9/2006 | Bodenteich et al. | |
| 2008/0226713 A1 | 9/2008 | Bodenteich et al. | |
| 2008/0274194 A1 | 11/2008 | Miller et al. | |
| 2009/0253743 A1 | 10/2009 | Gaeta et al. | |
| 2009/0298893 A1 | 12/2009 | Alken et al. | |
| 2010/0150995 A1 | 6/2010 | Welzig et al. | |
| 2010/0249423 A1 | 9/2010 | Welzig et al. | |
| 2010/0324090 A1 | 12/2010 | Gaeta et al. | |
| 2016/0367540 A1 | 12/2016 | Gaeta et al. | |

FOREIGN PATENT DOCUMENTS

| | | |
|---|---|---|
| AT | 500144 A1 | 11/2005 |
| AT | 413539 B | 3/2006 |
| AT | 505225 | 11/2008 |
| EP | 0717988 A1 | 6/1996 |
| GB | 2163648 A | 3/1986 |
| JP | 53-40779 | 4/1978 |
| JP | 54-27571 | 3/1979 |
| JP | 54-30178 | 3/1979 |
| JP | 54-32480 | 3/1979 |
| JP | 54-36274 | 3/1979 |
| JP | 4-5283 A | 1/1992 |
| WO | WO 2004/032927 A1 | 4/2004 |
| WO | WO 2004/050648 A1 | 6/2004 |
| WO | WO 2005/084676 A1 | 9/2005 |
| WO | WO 2005/094825 A1 | 10/2005 |
| WO | WO 2008/133937 A2 | 11/2008 |
| WO | WO 2009/013552 A1 | 1/2009 |

OTHER PUBLICATIONS

International Preliminary Report on Patentability for International Application No. PCT/US2008/005281 mailed Oct. 27, 2009, 6 pages.
"Tolperisone hydrochloride," ChemBook structure, 1 page (2012).
"Tolperisone," ChemBook structure, 1 page (2012).
Braga and Grepioni, "Making crystals from crystals: a green route to crystal engineering and polymorphism," Chem. Commun. 3635-3645 (2005).
Cheronis, "Purification of Solids by Crystallization," in Semimicro Experimental Organic Chemistry: A Laboratory Manual, pp. 31-43 (1958).
Davies, "Changing the salt, changing the drug," Pharm. J. 266(7138):322-323 (2001).
Dietrich and Fels, "Synthesis of $^3$H-Tolperisone," J. Label. Compounds Radiopharm. 42:1125-1134 (1999).
European Search Report for Appl. No. EP 10450026, 7 pages (Jul. 5, 2011).
International Search Report and Written Opinion for PCT appl. No. PCT/US2008/005281, 12 pages (Nov. 5, 2008).
International Search Report, PCT appl. No. PCT/AT2008/000149, 4 pages, (Mar. 11, 2009).

(Continued)

*Primary Examiner* — Layla Soroush
(74) *Attorney, Agent, or Firm* — Cooley LLP

(57) ABSTRACT

The present disclosure relates to methods of administering tolperisone to subjects in need thereof. In certain aspects, the present disclosure relates to methods of administering tolperisone to subjects in need thereof, said methods limiting the exposure of the subject to 4-MMPPO.

27 Claims, 2 Drawing Sheets

(56) References Cited

OTHER PUBLICATIONS

Li, et al.—"Investigation of Solubility and Dissolution of a Free Base and Two Different Salt Forms as a Funciton of pH", Pharmaceutical Research, vol. 22, No. 4, Apr. 2005, pp. 628-635.
Ono et al., "Mechanisms of Depressant Action of Muscle Relaxants on Spinal Reflexes: Participation of Membrane Stabilizing Action," J. Pharm. Dyn. 7(3):171-176 (1984).
Sae-Lee and Sae-Lee, "The Effect of Temperature on Stability of Tolperisone Hydrochloride Solution," Thai Pharm. Health Sci. J. 11(1):1-4 (2006).
Search Report in corresponding Austria Patent appl. No. A 1953/2007, 4 pages (dated Feb. 20, 2008).
Search Report in corresponding Austria Patent appl. No. A 658/2007, 4 pages (dated Feb. 19, 2008).
Seddon, "Pseudopolymorph: A Polemic," Crystal Growth & Design 4(6):1087 (2004).
Sumita et al., "A Modified Mannich Reaction Using 1,3-Dioxolane," Chem. Pharm. Bull. 42(8):1676-1678 (1994).
Sumita et al., Casreact Accession No. 122:264610, 10 pages (1994).
Ulrich, "Crystallization," in Kirk-Othmer Encyclopedia of Chemical Technology, vol. 8, pp. 95-147 (2002).
Velmurugan et al., "Optimization of the Reversed-Phase High-Performance Liquid Chromatographic Separation of the Enantiomers of a Cationic Chiral Drug (Tolperisone) on a Heptakis(6-Azido-6-deoxy) Perphenylcarbamated β-Cyclodextrin Column," Chromatographia 56(3-4):229-232 (2002).
Vippagunta et al. "Crystalline solids," Adv. Drug. Delivery Rev. 48:3-26 (2001).

METHODS OF ADMINISTERING TOLPERISONE FOR THERAPEUTIC PURPOSES

CROSS-REFERENCE TO RELATED APPLICATIONS

The present Application is a Divisional Application from U.S. application Ser. No. 12/597,664, which is a U.S. National Stage Application of International Application No. PCT/US2008/005281, each having a filing date of Apr. 24, 2008, and claiming the benefit of priority to Austrian Patent Application No. A 658/2007, filed on Apr. 26, 2007, and Austrian Patent Application No. A 1953/2007, filed on Nov. 29, 2007, and U.S. Provisional Application No. 61/023,799, filed on Jan. 25, 2008, the contents of each of which are herein incorporated by reference.

FIELD

The present disclosure relates generally to tolperisone, 2-methyl-1-(4-methylphenyl)-3-(-piperidinyl)-1-propanone), having extremely low levels of 4-MMPPO (2-methyl-1-(4-methylphenyl)-propenone), and methods of producing the same, as well as compositions related thereto. The invention further relates to methods of treating a subject with tolperisone under conditions that limit exposure of the subject to tolerable levels of 4-MMPPO, among other features.

BACKGROUND

Tolperisone is a centrally-acting muscle relaxant that has been used for the symptomatic treatment of spasticity and muscle spasm (Martindale, The Extra Pharmacopoeia, 30th ed., p. 1211). Tolperisone has also been used in the treatment of conditions which include dysmenorrhea, climacteric complaints, lockjaw, and neurolatyrism.

The chemical structure of tolperisone is shown below.

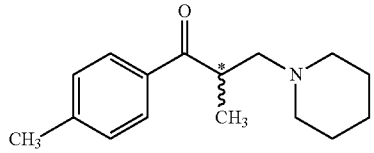 [SMILES: Cc1ccc(C(=O)C(C)CN2CCCCC2)cc1]

As can be seen by the foregoing structure, tolperisone contains a chiral center (as indicated by the asterisk). Racemic tolperisone is commercially available as the hydrochloride salt and is sold under trade names such as Mydeton®, Mydocalm®, Midocalm® and Muscalm®.

The chiral separation of tolperisone into its R(−) and S(+) enantiomers has been described (See, for example, JP-A-53-40779).

Tolperisone has been shown to exhibit membrane-stabilizing effects in the central and peripheral nervous system (Ono, H., et al., *J. Pharmacobio. Dynam.* 1984, 7, 171-178). Tolperisone and its salts are used for improving not only different symptoms related to spastic paralysis, but also for improving muscle tone which originates from diseases or conditions such as cervical syndrome, inflammation of the joints, and back pain. Recently, the use of tolperisone for treating neuropathic pain and pain associated with various nervous system disorders has also been described (see, for example, U.S. Patent Application No. 2006/0004050).

SUMMARY

Tolperisone can be prepared by a number of different synthetic approaches. As recognized by the inventors, as a result of side reactions and chemical impurities either present in the starting materials, or formed during the synthesis of tolperisone or over the shelf life of the formulation, current methods of producing tolperisone have the associated drawback of producing a final product that contains levels of impurities that can be toxic to patients undergoing treatment with tolperisone, even when present in extremely small quantities.

In one aspect, the present disclosure addresses the need for improved methods of providing tolperisone having negligible levels of impurities such as the genotoxic agent, 4-MMPPO. In another aspect, the present disclosure provides methods for treating subjects by administering tolperisone in which exposure to genotoxic agents such as 4-MMPPO in tolperisone-containing pharmaceutical compositions is minimized, among others.

Specifically, in at least one aspect, the disclosure is directed to tolperisone comprising less than about 10 ppm 2-methyl-1-(4-methylphenyl)-propanone (4-MMPPO) and compositions thereof.

In a particular embodiment, tolperisone as provided herein comprises less than about 7 ppm 4-MMPPO.

In yet another embodiment, tolperisone comprises less than about 3 ppm 4-MMPPO.

In a preferred embodiment, provided herein is tolperisone comprising from about 1.5 to 10 ppm 4-MMPPO.

Additionally, provided herein is a pharmaceutical composition comprising tolperisone as previously described and one or more a pharmaceutically acceptable excipients.

In one embodiment of the foregoing, said one or more pharmaceutically acceptable excipients comprises an acid.

In yet another aspect, provided herein is method of preparing a purified composition of tolperisone. The method comprises the steps of (i) providing tolperisone comprising an initial level of 4-MMPPO greater than 10 ppm, and optionally additional impurities, and (ii) purifying the tolperisone to form a purified tolperisone having a level of 4-MMPPO that is less than about 10 ppm.

In one embodiment of the foregoing method, the purifying step is effective to reduce the level of 4-MMPPO by at least five-fold over its initial level.

In yet another embodiment, purified tolperisone produced by the method has a level of 4-MMPPO of less than about 7 ppm, for example, having a purity as described above.

The method may also further comprise, prior to the providing step, identifying the presence of 4-MMPPO as a contaminant in the tolperisone, and optionally, determining the initial level of 4-MMPPO in the tolperisone.

In an additional embodiment of the method, the purifying comprises recrystallization from a single solvent or a combination of solvents to provide recrystallized tolperisone.

In another embodiment of the method, the recrystallization comprises either one or multiple recrystallization steps.

In yet another embodiment, the recrystallization is carried out in a mixed organic solvent system. In a particular embodiment, the solvent system comprises a lower ketone and a lower alcohol. In yet another embodiment, the solvent system comprises 2-butanone (methyl ethyl ketone) and isopropanol.

In a further embodiment, the recrystallization comprises dissolving tolperisone in an acidified solvent, optionally with heating, to form a solution of tolperisone, and allowing crystals of tolperisone to form from the solution.

In yet another alternative embodiment of the method, purifying comprises a drying step. The drying step may be carried out at atmospheric pressure or under reduced pressure. Drying may be carried out at ambient temperature or at elevated temperatures, e.g., from 30° C. to about 60° C.

In yet another aspect, provided herein is an improvement in a synthetic method for preparing tolperisone, where the improvement comprises addition of a catalytic amount of acid to thereby minimize formation of 4-MMPPO.

In a particular embodiment of the foregoing improvement, the acid is anhydrous hydrogen chloride gas.

Also provided herein is purified tolperisone, and compositions thereof, produced by the foregoing methods and all and any embodiments thereof.

In yet another aspect, provided herein is an improvement in a method of administering tolperisone to a subject in need thereof, where the improvement comprises administering a composition of tolperisone comprising less than about 10 ppm 2-methyl-1-(4-methylphenyl)-propanone (4-MMPPO), e.g., from about 1.5 to about 10 ppm 4-MMPPO.

In a particular embodiment of the foregoing, as a result of the administering, genotoxic effects of the composition related to the presence of 4-MMPPO upon the subject are minimized.

In yet another aspect, provided herein is tolperisone comprising less than about 10 ppm 4-MMPPO packaged in a suitable container, and combined with a dessicant.

In yet an additional aspect, provided herein is a method of detecting levels of 4-MMPPO in a composition comprising tolperisone. The method comprises the steps of (a) providing a composition comprising tolperisone and optionally one or more excipients, (b) dissolving the composition in acidified alcohol to thereby prevent formation of additional 4-MMPPO, to form an acidified solution of tolperisone, (c) separating said tolperisone from the one or more excipients, if present, by extraction with an organic solvent to provide an acidified extract of tolperisone, (d) adding to the solution of (b) or (c) an internal standard to quantify the amount of 4-MMPPO to provide a sample solution, and (e) analyzing the amount of 4-MMPPO in the sample solution by liquid chromatography/mass spectrometry, wherein at least one eluent employed in said liquid chromatography is acidified, to thereby detect levels of 4-MMPPO in said sample that may be below 500 ppm.

In one embodiment of the foregoing method, the acidified alcohol is acidified with hydrochloric acid. In a particular embodiment, the acidified alcohol is methanolic hydrochloric acid.

In yet another embodiment of the method of detecting, the organic solvent in (c) is an ether.

In yet another embodiment, the solvent is diisopropyl ether.

In yet another embodiment, the internal standard is deuterated MMPPO.

Additional embodiments of the present method, compositions, and the like will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

Figure 1:
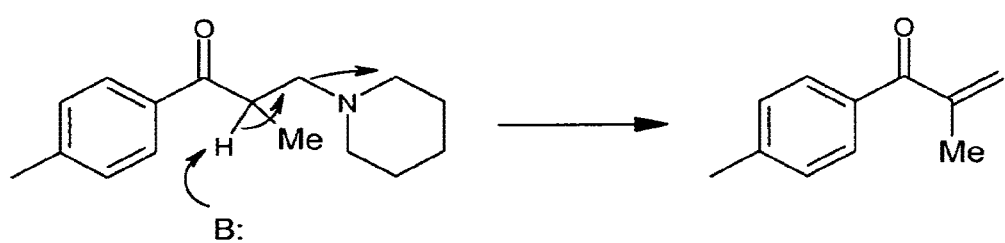
FIG. 1 shows a proposed chemical mechanism for formation of 4-MMPPO from tolperisone via a β-elimination reaction.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

All publications, patents and patent applications cited herein, whether supra or infra, are hereby incorporated by reference in their entirety.

DEFINITIONS

It must be noted that, as used in this specification, the singular forms "a," "an," and "the" include plural referents unless the context clearly dictates otherwise.

In describing and claiming the present invention, the following terminology will be used in accordance with the definitions described below.

The term, tolperisone, as well as reference to other chemical compounds herein, is meant to include the compound in any of its pharmaceutically acceptable forms, including isomers such as diastereomers and enantiomers, salts, solvates, and polymorphs, particular crystalline forms, as well as racemic mixtures and pure isomers of the compounds described herein, where applicable.

"Pharmaceutically acceptable excipient or carrier" refers to an excipient that may optionally be included in the compositions of the invention and that causes no significant adverse toxicological effects to the patient upon administration.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

The term, "alkyl", refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include methyl, ethyl, propyl, isopropyl, butyl, pentyl, 1-methylbutyl, 1-ethylpropyl, 3-methylpentyl, and the like. As used herein, "alkyl" includes cycloalkyl when three or more carbon atoms are referenced.

"Lower" in reference to a particular functional group means a group having from 1-6 carbon atoms.

For example, "lower alkyl" refers to an alkyl group containing from 1 to 6 carbon atoms, and may be straight chain or branched, as exemplified by methyl, ethyl, propyl, isopropyl, 1-ethylpropyl, 1,2-dimethylpropyl, n-butyl, i-butyl, sec-butyl, t-butyl, and the like.

"Optional" or "optionally" means that the subsequently described circumstance may or may not occur, so that the description includes instances where the circumstance occurs and instances where it does not.

"Substantially absent" or "substantially free" of a certain feature or entity means nearly totally or completely absent the feature or entity. As used herein, a toloperisone formulation that is substantially absent 4-MMPPO contains less than about 10 ppm 4-MMPPO.

A tolperisone composition that has been stored under "dry conditions" is one that has been stored under controlled humidity conditions (5-25 percent relative humidity) and at temperatures ranging from about 18-25° C. The tolperisone composition may be the active pharmaceutical ingredient (API), or a pharmaceutical composition (powder or the like) comprising tolperisone and one or more pharmaceutically acceptable excipients, or a finished product, for example, a capsule, tablet, etc. The composition is contained in a sealed container such as a bottle, blister, pouch, or a combination thereof. The composition may also be stored in the presence of a dessicant, such as silica, typically encased in a pak suitable for absorption of water vapor.

"Anhydrous" refers to a material that is substantially absent water.

The terms "subject", "individual" or "patient" are used interchangeably herein and refer to a vertebrate, preferably a mammal. Mammals include, but are not limited to, humans.

The terms "pharmacologically effective amount" or "therapeutically effective amount" of a tolperisone composition as provided herein, refer to a non-toxic but sufficient amount of the composition or agent to provide the desired response, e.g., improving symptoms related to spastic paralysis or for treating neuropathic pain and pain associated with various nervous system disorders has also been. The exact amount required will vary from subject to subject, depending on the species, age, and general condition of the subject, the severity of the condition being treated, additional drugs being taken by the subject, mode of administration, and the like. An appropriate "effective" amount in any individual case may be determined by one of ordinary skill in the art using routine experimentation, based upon the information provided herein.

The term "about", particularly in reference to a given quantity, is meant to encompass deviations of plus or minus five percent.

Additional definitions may also be found in the sections which follow.

Overview

As described above, the present disclosure addresses the need to provide formulations of tolperisone in which the levels of 4-MMPPO are significantly and preferably consistently reduced over those found in commercial formulations, or those previously described. In preparing or obtaining and analyzing tolperisone compositions, in particular by devising an extremely sensitive assay for detecting low levels of 4-MMPPO, e.g., in tolperisone formulations, the inventors recognized the need to provide formulations of tolperisone with improved purity, particularly with respect to the genotoxic agent, 4-MMPPO. As a result, formulations as described herein are administered to a subject for treatment of a condition responsive to treatment with tolperisone, such that, as a result of such administering, genotoxic effects associated with the presence of 4-MMPPO in said tolperisone are minimized. These and other aspects of the invention will now be described in greater detail below.

Features of the Method

Toloperisone and Related Impurities

Tolperisone, also referred to as 2-methyl-1-(4-methylphenyl)-3-(-piperidinyl)-1-propanone, possesses the chemical structure shown below.

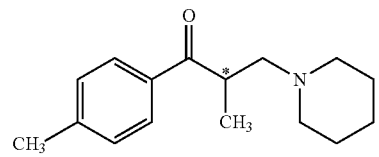 [SMILES: Cc1ccc(C(=O)C(C)CN2CCCCC2)cc1]

Tolperisone contains a chiral center (as indicated by the asterisk in the foregoing structure). Racemic tolperisone is commercially available as the hydrochloride salt and is sold under trade names such as Mydeton®, Mydocalm®, Midocalm® and Muscalm®. Reference herein to tolperisone is meant to encompass racemic tolperisone, each of its enantiomers, mixtures thereof in any proportion, as well as pharmaceutically acceptable salts, various crystalline forms, and hydrates thereof.

In addition to being obtained commercially, tolperisone can be synthesized by a variety of methods known in the art. See, e.g., U.S. Patent Application Publication No. 2006/0041141; Ditriech et al. (1999) *J. Labeled Cpd. Radiopharm*, 42:1125-1134; Jap. Pat. No. 04005283 19920109; Jap. Pat. No. 54032480 19790309; Jap. Pat. No. 54036274 19790316; Jap. Pat. No. 54030178 19790306; Jap. Pat. No. 54027571 19790301; Kazuharu et al. (1994) Chem. Pharm. Bulletin 42(8) 1676; Jap. Pat. No. 20,390 (1965); and Hung. Pat. No. 144,997 (1956), each incorporated herein by reference in its entirety.

Tolperisone may, for example, be prepared according to the following single step synthesis scheme:

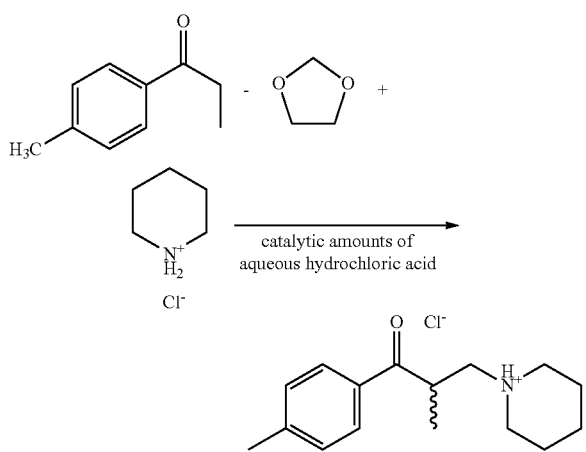

where 4-methylpropiophenone is used as the starting material. In the exemplary reaction above, 1,2-dioxolane acts as both reactant and solvent. The use of 1,2-dioxolane in place of formaldehyde, and the high yield after direct isolation of the tolperisone crude product make the single-stage reaction particularly advantageous, e.g., due to its cost-effectiveness on an industrial scale, among other reasons. See, e.g., U.S. 2006/0041141.

In instances in which a particular enantiomer is desired, e.g., either or both of the R(−) and S(+) enantiomers, a chiral separation may be carried out, e.g., as described in JP-A-53-40779. Chiral separation may also be conducted as described in Velmurugan, et al., *Chromatorgraphia*, 56 (3-4), August 2002, 229-232. Velmurugan describes reverse phase-HPLC separation of tolperisone into each of its enantiomers.

Depending on the synthesis strategy employed, compositions of tolperisone may include any one or more of the following impurities: piperidine hydrochloride, 2-methyl-1-(3-methylphenyl)-3-(1-piperidinyl)-propanone hydrochloride (3-tolperisone hydrochloride), 1-(4-methylphenyl)-propanone (4-methylpropiophenone), 2-methyl-1-(4-methylphenyl)-propenone (4-MMPPO), and 2-methyl-1-(2-methylphenyl)-3-(1-piperidinyl)-propanone hydrochloride (2-tolperisone hydrochloride). U.S. Patent Application No. US 2006/0041141 describes a synthesis method for significantly reducing the content of the isomers, 2-tolperisone and 3-tolperisone, in preparations of 4-tolperisone to form tolperisone having a final purify with respect to these isomers that is substantially improved over prior formulations. However, to the inventors' knowledge, heretofore, formulations such as those described herein, that are substantially absent 4-MMPPO, and/or stabilized against formation of the degradant, 4-MMPPO, have not been provided, or have not been provided in a reliable, consistent fashion. Nor has the significance of formulations such as those provided herein been previously recognized. The instant formulations are extremely advantageous for administration, since in vivo exposure to 4-MMPPO in a subject undergoing treatment with tolperisone should be kept below stringent levels, due to the genotoxic effects associated with 4-MMPPO.

Figure 2:
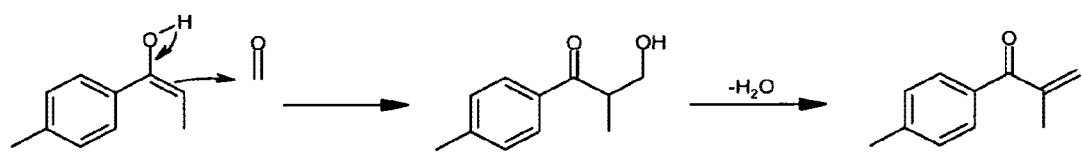
FIG. 2 shows a proposed chemical mechanism for formation of 4-MMPPO via a β-elimination of a γ-hydroxyketone side product of tolperisone.

Without being bound by theory, it is believed that the compound, 4-MMPPO, is likely formed via a β-elimination reaction as demonstrated mechanistically in FIG. 1. Depending upon the synthesis conditions, 4-MMPPO may also form via β-elimination of water from a potential side-product, a γ-hydroxyketone, formed from an aldol-condensation reaction as shown in FIG. 2. The structure of 4-MMPPO is provided below.

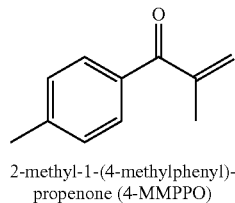

2-methyl-1-(4-methylphenyl)-
propenone (4-MMPPO)

Thus, 4-MMPPO may be formed as a side-product during the synthesis of tolperisone, or alternatively, may form during storage of tolperisone, when stored either solely (i.e., as active agent per se, commonly referred to as an "API" or "active pharmaceutical ingredient"), or as part of a pharmaceutical formulation (i.e., in combination with one or more pharmaceutically acceptable excipients). Additionally, 4-MMPPO may form during the dissolution or heating phase of a recrystallization procedure employed to purify the API. Typically, most of any such 4-MMPPO formed will remain in the mother liquor(s), although small amounts may remained associated with the recrystallized tolperisone. After collection of the recrystallized tolperisone, a subsequent drying step may also facilitate formation of 4-MMPPO, particularly at elevated temperatures.

Analysis

In arriving at the tolperisone formulations provided herein, the inventors devised an optimized analytical method to detect extremely low levels of 4-MMPPO, where the method is capable of levels of detection below about 0.05% weight (500 ppm) 4-MMPPO. Preferably, the method is capable of detecting levels below about 400 ppm, or even below 300 ppm. Even more preferably, the method is capable of detecting levels of 4-MMPPO below about 200, or even 100 ppm. It is believed that the methods provided herein are capable of detecting extremely low levels of 4-MMPPO, e.g., less than about 50 ppm, or even less than 25 ppm, and more preferably less than about 10 ppm 4-MMPPO. In the examples provided herein, levels less than about 9 ppm, less than about 8 ppm, less than about 7 ppm, less than about 6 ppm, less than about 5 ppm, less than about 4 ppm, less than about 3 ppm, less than about 2 ppm, less than about 1.5 ppm, or even less than 1 ppm are detectable. It is believed that the present method is capable of detecting levels of 4-MMPPO down to about at least 0.5 ppm.

The method employed is based upon a combination of liquid chromatography-mass spectrometry (LC-MS). The present method overcomes the disadvantages of prior methods unable to detect 4-MMPPO at levels below about 500 ppm. Since 4-MMPPO is a genotoxic agent, its detection to levels significantly below 500 ppm is extremely important, as producers of tolperisone must be able not only to quantify the content of potential genotoxins such as 4-MMPPO in pharmaceutical formulations, but must also be able to demonstrate that compositions containing even negligible amounts of such genotoxins lack a genotoxic hazard when administered.

Generally, the method involves providing a composition of tolperisone. The tolperisone may be crude tolperisone formed during a synthetic reaction, purified tolperisone submitted to one or more purification steps, tolperisone obtained from a commercial source or a toll manufacturer, or extracted from a pharmaceutical formulation such as a tablet (e.g., Mydeton®, Mydocalm®, Midocalm® and Muscalm®) or other delivery form. For pharmaceutical formulations such as tablets, the sample is typically first homogenized with a suitable solvent to break up the tablet formulation and provide a uniform solution or suspension of the formulation components, thereby making extraction of tolperisone (and any associated 4-MMPPO) more facile. Suitable solvents for homogenization include anhydrous isopropanol acidified with about 1% HCl gas or about 1% anhydrous trifluoroacetic acid (TFA).

The tolperisone is dissolved in a suitable solvent system, such as an acidified alcohol. Illustrative solvents include methanol, isopropanol, butanol and other lower alcohols. Acids that may be employed to acidify the solvent include, e.g. hydrochloric acid, hydrobromic acid, citric acid, formic acid, acetic acid, methanesulfonic acid, and trifluoroacetic acid, among others. The inventors have recognized, in their various attempts at analyses, that acidified conditions can be used to prevent additional base-catalyzed formation of 4-MMPPO, and stabilize the tolperisone during its analysis—thereby providing a more accurate reflection of the 4-MMPPO content in the sample. Preferably, the solvent(s) used to dissolve/suspend the sample is anhydrous, since the presence of even small amounts of water may lead to increased formation of 4-MMPPO. One preferred acidified alcoholic solution is methanolic HCl. The concentration of acid in the alcohol typically ranges from about 10 mM to about 100 mM and is effective to stabilize the tolperisone against further degradation to 4-MMPPO. In instances in which the tolperisone is part of a pharmaceutical formulation such as a tablet, tolperisone may be extracted from any binders, fillers, excipients, and the like that may be contained in the formulation, e.g., by extraction with an organic solvent. Solvents that may be employed are preferably acidified alcoholic solvents such as those described above, although other solvents may be employed as well, such as ethers or lipophilic esters. Particular solvents that may be suitable include dichloromethane, chloroform, acetonitrile, amyl acetate, and dioxane.

Prior to analysis, an internal standard is typically added to the sample. In the present method, a preferred standard is deuterated 4-MMPPO, such that the standard can be readily differentiated from 4-MMPPO contained in the sample. The internal standard employed will of course vary with the method of detection employed. Preferably, a buffer is added to the solution to be analyzed to maintain an acidic solution. Illustrative buffers include citrate, phosphate, and acetate. Preferably, the pH of the solution is below 5.5, and even more preferably is below 4. Suitable pHs for the solution to be analyzed are 5.5 or below, 5 or below, 4.5 or below, 4 or below, 3.5 or below, 3 or below, 2.5 or below, 2 or below, 1.5 or below, or 1.0 or below.

The sample is then analyzed for 4-MMPPO content. Although a number of analytical techniques can be employed for analysis, e.g., nuclear magnetic resonance (NMR), gas chromatography (GC), mass spectrometry (MS), and combinations thereof, such as LC (liquid chromatography)/MS, GC/MS, GC/MS with negative chemical ionization, GC/MS/MS, MS/MS/LIT (linear ion trap), high performance liquid chromatography, HPLC/MS/MS, FT/IR (fourier transform infrared) and the like, a preferred method is liquid chromatography/mass spectrometry/mass spectrometry (LC/MS/MS), in particular HPLC/MS/MS.

Different methods may be employed to obtain the mass spectra, including time-of-flight (TOF), quadrupole, ion trap, magnetic sector, and combinations of the foregoing. Tandem quadrupole mass spectrometry (MS/MS) is preferred, due to its high signal-to-noise ratio (S/N). The method described herein, e.g., in Example 1, is capable of achieving a level of detection of 4-MMPPO of below 500 ppm, to levels down to about 0.2 ppm.

For analytical methods employing HPLC, solvents for use as eluents include water, alcohols such as methanol, ethanol, isopropanol, acetonitrile, and combinations thereof. Preferably, at least one solvent employed as the mobile phase is acidified, to minimize formation of additional 4-MMPPO during the analysis. Suitable acids include formic acid, hydrochloric acid, phosphoric acid, trifluoroacetic acid, and the like. HPLC columns can be obtained from a number of commercial suppliers, such as PerkinElmer, EMScience, Phenomenex, and the like. For instance, columns such as those prepared by Shiseido, Shodex, Agilent (ZORBAX), and LUNA can be employed as the solid support. Normal or reversed phase columns can be used; preferred solid supports include silica gel. Conditions for obtaining separation of components and quantification of contaminants such 4-MMPPO can be determined by one of skill in the art.

Example 1 herein provides exemplary experimental conditions for analysis of tolperisone-containing formulations to determine 4-MMPPO content (Tables 1 and 2). The analytical method described herein allows quantification of 4-MMPPO to levels undetectable by previous methods. As can be seen by the values provided in Table 3, values of 4-MMPPO in various representative formulations (both API and commercial pharmaceutical formulations) were discovered to range from about 15 ppm to over 400 ppm. Commerical formulations Mydeton® and Mydocalm® all possessed levels of 4-MMPPO that were in excess of 100 ppm. Due to the genotoxic side effects associated with 4-MMPPO, the inventors recognized a need to provide formulations having substantially lower levels of 4-MMPPO than those detected for the formulations in Table 3, i.e., below about 10 ppm.

Purification

The inventors recognized a need to provide tolperisone compositions of a greater purity with respect to 4-MMPPO than have been previously prepared, preferably in a consistent manner. In this regard, various approaches were explored to achieve tolperisone formulations containing less than about 10 ppm 4-MMPPO. The methods described herein are capable of providing tolperisone with a level of 4-MMPPO that is less than about 10 ppm. Tolperisone formulations as provided herein will thus contain less than about 10 ppm 4-MMPPO, less than about 9 ppm, less than about 8 ppm, less than about 7 ppm, less than about 6 ppm, less than about 5 ppm, less than about 4 ppm, less than about 3 ppm, even less than about 2 ppm. In a preferred embodiment, tolperisone as provided herein contains from about 1.5 ppm to about 10 ppm 4-MMPPO.

Recrystallization—Single Stage

Typically an "impure" tolperisone composition for purification as set forth herein will contain greater than about 10 ppm 4-MMMPPO. One method that is particularly useful for removing trace amounts of 4-MMPPO is recrystallization. Example 2 describes a conventional recrystallization approach for purifying tolperisone. As can be seen, dissolution of tolperisone in an organic solvent mixture (accomplished by heating to reflux), followed by hot filtration and cooling of the filtrate results in formation of crystalline tolperisone. Analysis of 4-MMPPO content in the recrystallized product revealed about 0.14 percent by weight tolerpisone (1400 ppm), which was reduced in subsequent recrystallized batches to about 500 ppm or somewhat below. However, the level of 4-MMPPO was unsuitable for pharmaceutical compositions of tolperisone.

However, single stage recrystallization may be suitable for providing tolperisone having the purity described herein when combined with one or more additional approaches for minimizing or inhibiting formation of 4-MMPPO as described in detail in the sections which follow.

Multiple Stage Recrystallization

Exploration of alternative recrystallization methods revealed the following approaches for providing purified tolperisone that is substantially absent of 4-MMPPO.

In one recrystallization approach, single stage recrystallization is carried out. In certain instances, tolperisone having the desired purity may be achieved in a single recrystallization. See, e.g., Example 3.

In another approach, multiple stage recrystallization is carried out. For example, tolperisone containing significant amounts of 4-MMPPO, i.e., greater than about 10 ppm, is submitted to multiple recrystallizations, i.e., more than 1 recrystallization, preferably 2 or more recrystallizations, to provide tolperisone that is substantially absent 4-MMPPO.

Typically, the number of recrystallizations is selected from 2, 3, 4, 5, and 6. Ideally, the desired purity is achieved in 2, 3 or 4 recrystallization steps. Solvents for use in recrystallizing tolperisione include single solvents as well as mixed solvent systems. A mixed solvent system may contain a combination of two solvents, three solvents, four solvents, five solvents or more, but preferably will contain two to four different solvents. Such solvents may optionally be acidified. Use of an acidified solvent may be effective in suppressing beta elimination reactions, since such reactions are base-catalyzed.

Solvents for use in recrystallizing tolperisone include esters such as ethyl acetate, methyl acetate, amyl acetate, ethers, preferably lower alkyl ethers such as diethyl ether, methyl tert-butyl ether (MTBE), ketones, preferably lower alkyl ketones such as 2-butanone, (methyl ethyl ketone, or MEK), methyl isobutyl ketone (MIBK), methyl propyl ketone, acetone, and the like, and alcohols. Preferred are lower alcohols such as methanol, ethanol, isopropanol, and the like. Mixtures of any of the foregoing may be employed. One preferred solvent system combines a lower ketone and a lower alcohol, e.g., methyl ethyl ketone and isopropanol. Typically, tolperisone is first dissolved in one or more recrystallization solvents. In certain instances, depending upon the solvent(s) employed, heat may be used to aid in dissolution of tolperisone in the solvent system. Preferably, a solvent system is employed in which tolperisone dissolves to an extent of about 100 mg/ml to about 200 mg/ml. Depending upon the boiling points of the solvents employed, a solution of tolperisone may be heated to about 80° C., if desired. Agitation may also be employed to aid in dissolution. The resulting solution is then typically allowed to cool, if heated, to room temperature or below. Ideally, cooling is done slowly, over a period of minutes or one or more hours, up to several hours. In certain instances, an ice-bath may be employed to further cool the tolperisone solution. During crystal formation, the solution may optionally be stirred. A seed crystal may also be added to induce crystal formation.

Crystals are collected and then washed with a suitable solvent, e.g., one in which tolperisone is insoluble or only negligibly soluble. One solvent for use is 2-butanone, preferably cold 2-butanone.

The crystals are then dried. Preferred drying conditions are described in the section below entitled, "Drying". Drying will typically be carried out at either ambient temperatures or at slightly elevated temperatures, from about 30° C. to about 45° C., preferably from about 30° C. to about 40° C.

The resulting purified tolperisone is then typically analyzed as described above to determine 4-MMPPO content. For tolperisone compositions possessing greater than about 10 ppm of 4-MMPPO, repeated recrystallizations are carried out as described above. See Example 3.

Acid Treatment

Due to the realization that 4-MMPPO formation can be suppressed in the presence of acid, preferred methods of purification include treatment of tolperisone with acid. For example, recrystallized tolperisone may be washed with an acidic solution, e.g., a solution containing from about 10% (v/v) to about 0.5% acid, preferably from about 7% (v/v) to about 1% (v/v) acid. Inorganic acids such as hydrochloric acid, hydrobromic acid, and sulfuric acid may be used; organic acids such as formic acid, oxalic acid, acetic acid, citric acid, trifluoroacetic acid, toluenesulfonic acid, benzenesulfonic acid, naphthalenesulfonic acid, succinic acid, and the like may also be employed. The acid solution may be an aqueous solution of acid, or alternatively, may be an acidified solvent such as an acidified alcohol as long as the acidified solution is one in which tolperisone is insoluble or only slightly soluble. One such exemplary solvent system is HCl/isopropanol. See, e.g., Example 4. It has been discovered that treatment of tolperisone with acid (either during synthesis or post-synthesis) is effective to substantially lower the levels of 4-MMPPO in the tolperisone product, such that tolperisone that is substantially absent 4-MMPPO is obtained.

As an alternative to an acid wash, recrystallization as described above may be carried out using an acidified solvent/solvent system. Exemplary recrystallizations of tolperisone using an acidified solvent system are provided in Examples 5 and 6. Single or multiple recrystallizations may be employed. Preferably, an acid such as one or more of those described above is added to the recrystallization solvent/solvent system. An amount of acid effective to acidify the solution while not destroying to any significant extent the active agent, tolperisone, is employed. Preferably, acid is added to the recrystallization solution to a total weight/volume percent ranging from about 10 percent to about 0.5 percent acid, preferably from about 5 percent to about 1 percent (w/v). Illustrative amounts of acid include 5, 4, 3, 2, and 1% acid (w/v). Typically, the solvent system employed will contain about 1% (w/v) acid. Recrystallization under acidified conditions tends to prevent 4-MMPPO formation, and provide purified tolperisone that is substantially absent 4-MMPPO.

In certain instances, where the tolperisone is either subjected to an acid wash or recrystallized from an acidified solvent, it may be preferable to employ an acidified solvent that is dry—i.e., that is substantially absent water. For example, dry HCl gas may be bubbled into a solvent system where the solvent is essentially anhydrous, to provide an acidified solvent system that is anhydrous or nearly so. Additional acids include citric acid, trifluoroacetic acid, and succinic acid. In certain studies, the inventors have observed increased levels of 4-MMPPO that may be attributable to the presence of water—such that the use of anhydrous conditions may be preferred.

Drying

In yet another approach to providing tolperisone that is substantially absent 4-MMPPO, tolperisone, preferably tolperisone that has been purified as previously described, is dried over an extended period of time ranging from one hour to several hours. Typical drying periods can extend from one hour to several hours, such as 72 hours or more. Drying can be carried out at room temperature and pressure, and may be carried out over a dessicant such as phosphorous pentoxide. Drying may take place at elevated temperatures such as in a drying oven, preferably at temperatures from about 30° C. to about 40° C. Drying may also take place under reduced pressure (optionally accompanied by gentle heating as described above), e.g., under low vacuum (e.g., from about 100,000 to about 3,000 Pascal), medium vacuum (from about 3,000 to about 0.1 Pascal) or even high vacuum (from about 0.1 to about 0.0001 Pascal). The drying process is effective to selectively remove 4-MMPPO from tolperisone by evaporation (volatilization). Due to the difference in volatility between tolperisone and 4-MMPPO, 4-MMPPPO can be selectively removed from the composition. Removal of 4-MMPPO by volatilization can similarly be carried out using a vacuum oven, paddle drier, fluid bed drier, flash drier, tray drier, spray drier, or any other similar drying technology, optionally at somewhat elevated temperatures, e.g., from about 30° C. to about 40° C.

As a result of the purification methodologies described above, in certain instances, depending upon the initial amount of 4-MMPPO contained in the tolperisone, the amount of 4-MMPPO removed is reduced dramatically, i.e., by at least five-fold over its initial level. For example, in turning to Example 3, it can be seen that a composition of tolperisone containing an initial amount of 4-MMPPO of greater than about 500 ppm was purified to form a purified tolperisone containing from about 1.5 ppm to about 10 ppm 4-MMPPO—a reduction of from about 50 times (50×) to about 300 (300×) times that of the original composition. Thus, depending upon the initial amount of 4-MMPPO, the purification methods provided herein can be effective to reduce the amount of 4-MMPPO by at least about 5-fold (or 5×), or at least about 10-fold, or at least about 20-fold, or at least about 30-fold, or at least about 50-fold, or at least 100-fold or more, in the resulting purified composition.

During Synthesis

Alternatively, rather than purify tolperisone post-synthesis as described above, to remove 4-MMPPO, modified syntheses may be carried out under certain modified reaction conditions. Such conditions include the use of acidified and/or anhydrous reaction conditions.

For example, the synthesis of tolperisone as described above can be carried out in the presence of a catalytic amount of acid. Acids suitable for such use include HCl (preferably gaseous), sulfuric acid, and nitric acid, formic acid, oxalic acid, acetic acid, citric acid, and the like.

Anhydrous conditions can be favored by the use of dry solvents, such as those obtained directly from a still and maintained over a drying agent, or solvents stored over molecular sieves or the like, and stored under an inert, dry atmosphere. Anhydrous reaction conditions can be further promoted by carrying out the synthesis under a dry inert atmosphere, such as nitrogen or argon.

That is to say, tolperisone may be synthesized by any of the routes described herein, or previously known, with the exception that, as an improvement, tolperisone is formed in the presence of a catalytic amount of acid and/or under anhydrous conditions.

Storage of Tolperisone

Example 7 provides data comparing the amount of 4-MMPPO contained in a drug lot used to make a tabletted pharmaceutical formulation, versus the amount of 4-MMPPO contained in the tablets after storage for a period ranging from 3 months to nearly 4 years. In nearly all of the formulations examined, a notable increase in the amount of 4-MMPPO was observed. While formation of 4-MMPPO may be attributable, at least in part, to conditions under which the tablets were prepared, it also seems likely that 4-MMPPO is formed in the pharmaceutical formulation over its shelf life, i.e., upon storage. Regardless of the origination of formation of 4-MMPPO, pharmaceutical formulations of tolperisone for administration to a subject should ideally contain significantly lower levels of 4-MMPPO than those in Example 7, and preferably, should contain levels of 4-MMPPO that are less than about 10 ppm. Even more preferably, a pharmaceutical formulation of tolperisone contains less than about 9 ppm, less than about 8 ppm, less than about 7 ppm, less than about 6 ppm, less than about 5 ppm, less than about 4 ppm, less than about 3 ppm, less than about 2 ppm, to about 1.5 ppm 4-MMPPO.

Preferably, tolperisone and tolperisone compositions as described herein are stored under dry conditions. Dry conditions as used herein refers to a temperature ranging from about 18 to 23° C. and a relative humidity of 5-25%. The subject formulation may be an API formulation, a pharmaceutical composition comprising in addition to the API, one or more pharmaceutically acceptable excipients, or a pharmaceutical formulation for administration that is contained in a sealed container such as a bottle, blister pack, pouch, or a combination thereof. The composition may also be stored in the presence of a dessicant, such as silica, typically encased in a pak suitable for absorption of water vapor.

Preferably, a tolperisone composition as provided herein comprises tolperisone in the form of an acid addition salt. In a preferred embodiment, a tolperisone composition as provided herein will also comprise an additional amount of an acidic additive or excipient to establish an environment that is more acidic than that provided by tolperisone in the form of an acid addition salt. Such additives include acetic acid, succinic acid, adipic acid, propionic acid, citric acid, toluenesulfonic acid, methanesulfonic acid, and the like. Preferred acids are di-acids or greater (e.g., di-acids, tri-acids, etc., having more than one acidic proton. Preferably, acids for use as stabilizers for compositions of tolperisone will possess a pKa of less than about 3. Preferably, the acid is anhydrous. Particularly preferred acids include citric acid and succinic acid.

Tolperisone may be combined within a glassy matrix; glass formers are well known in the art, and may be effective in preventing chemical degradation of tolperisone to 4-MMPPO.

Ideally, tolperisone, irrespective of its formulation, is combined with a dessicant during storage, such that its exposure to moisture is minimized.

Genotoxicity of 4-MMPPO

4-MMPPO is considered genotoxic, that is, capable of causing genetic mutation and potentially contributing to the development of tumors. Genotoxicity is generally considered to be an intrinsic property of certain chemical agents. Based upon a compound's chemical structure, the compound may possess sufficient electrophilicity to bind with nucleophilic sites in cellular macromolecules such as DNA.

Ideally, tolperisone compositions provided herein, when evaluated in genetic toxicology studies, indicate a lack of genotoxic potential—due at least in part to the extremely low levels of 4-MMPPO contained therein. Genetic toxicology studies suitable to assessing genotoxic hazard include the following rodent in vitro assays: a test for gene mutation in bacteria 3B, an in vitro assessment of chromosomal damage using mammalian cells or an in vitro mouse lymphoma tk$^{+/-}$ assay, and an in vivo test for chromosomal damage using rodent hematopoietic cells. Alternative models for assessing carcinogenicity can be found in ICH guidance for industry *S1B Testing for Carcinogenicity of Pharmaceuticals*.

In vivo assays may also be used to further indicate a lack of genotoxic potential, especially in instances in which results from an in vitro study may suggest a potential genotoxic hazard. In vivo assays that may be employed to indicate a lack of genotoxicity of the tolperisone compostions provided herein include the following. For example, peripheral blood smears from repeat dose toxicity studies in mice may be evaluated for micronucleus induction. Peripheral blood lymphocytes from repeat dose studies in rats or monkeys can be cultured and assessed for chromosome damage in metaphase spreads. Additionally, DNA damage (e.g., (DNA adducts or DNA strand breakage using the Comet or alkaline elution assay) can be assessed in potential target tissues. Transgenic rats or mice can also be used to assess mutagenicity in potential target tissues.

The Syrian hamster embryo cell (SHE) transformation assay may also be used. Further, transgenic mouse strains such as the p53 haplo insufficient mouse may be used in short-term carcinogenicity studies.

A substantial absence of genotoxic side effects (or genotoxicity) of a formulation as provided herein, in reference to a tolperisone composition comprising less than about 10 ppm 4-MMPPO when administered to a subject at a pharmaceutically acceptable dose, is indicated based upon a negative result in at least one of the three in-vitro studies described above. Preferably, at least two of the in-vitro assays are negative, and even more preferably, all three of the in-vitro assays are negative with respect to genotoxicity. In instances in which one or more of the in-vitro studies described above provides a positive or less than conclusive result in terms of lack of genotoxicity, a negative result in one or more of the above-described in-vivo studies may be relied upon to demonstrate a lack of genotoxicity.

Pharmaceutical Formulation Components

In addition to comprising tolperisone, a formulation of the invention may optionally contain one or more additional components.

A composition of the invention may comprise, in addition to tolperisone, one or more pharmaceutically acceptable excipients or carriers. Exemplary excipients include, without limitation, polyethylene glycol (PEG), hydrogenated castor oil (HCO), cremophors (polyethoxylated castor oil), carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

A composition of the invention may include one or more carbohydrates such as a sugar, a derivatized sugar such as an alditol, aldonic acid, an esterified sugar, and/or a sugar polymer. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Also suitable for use in the compositions of the invention are potato and corn-based starches such as sodium starch glycolate and directly compressible modified starch.

Further representative excipients include inorganic salts or buffers such as citric acid, sodium chloride, potassium chloride, sodium sulfate, potassium nitrate, sodium phosphate monobasic, sodium phosphate dibasic, and combinations thereof.

A tolperisone composition may also include an antimicrobial agent, e.g., for preventing or deterring microbial growth. Non-limiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

A composition as provided herein may also contain one or more antioxidants. Antioxidants are used to prevent oxidation, thereby preventing the deterioration of the tolperisone or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, as described previously, a composition of the invention may optionally include one or more acids. Non-limiting examples of acids that can be used include those acids selected from the group consisting of hydrochloric acid, acetic acid, phosphoric acid, citric acid, succinic acid, adipic acid, propionic acid, toluenesulfonic acid, methanesulfonic acid, malic acid, lactic acid, formic acid, trichloroacetic acid, nitric acid, perchloric acid, phosphoric acid, sulfuric acid, fumaric acid, and combinations thereof.

In a preferred embodiment, a composition as provided herein is absent a basic component.

The amount of any individual excipient in the composition will vary depending on the role of the excipient, the dosage requirements of the active agent (i.e., tolperisone), and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient. In general, the amount of excipient present in a tolperisone composition of the invention is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

Exemplary formulations for administration are those currently on the market, e.g., Mydeton®, Mydocalm®, Midocalm® and Muscalm®, and similar such formulations. A formulation for oral administration may, for example, contain from about 50 to about 750 mg of tolperisone, preferably from about 100 to about 500 mg of tolperisone. For example, formulations for oral administration may, in certain instances, contain any one of the following amounts of tolerperisone: 100 mg, 150 mg, 200 mg, 250 mg, 300 mg, 350 mg, 400 mg, 450 mg, or 500 mg of tolperisone.

Tolperisone may be provided in a sustained-release formulation. See, e.g., Example 9, and International Patent Publication No. WO 2005/094825. Controlled or sustained-release formulations are typically prepared by incorporating tolperisone into a carrier or vehicle such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures.

One exemplary controlled release formulation includes a mixture of anionic and cationic polymers, such as Eudragit RS, Eudragit L and Eudragit S. Additionally, tolperisone can be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; and McGee et al., *J.*

*Microencap.* (1996). Tablets or caplets may also be coated with water insoluble polymers, e.g., Aquacoat® and Eudragit®.

The foregoing pharmaceutical excipients along with other excipients are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

Pharmaceutical Formulations/Delivery Forms

The tolperisone described herein may be formulated into any form suitable for administration. Oral dosage forms include tablets, lozenges, capsules, syrups, oral suspensions, emulsions, granules, and pellets. Alternative formulations include aerosols, transdermal patches, gels, creams, ointments, suppositories, powders or lyophilates that can be reconstituted, as well as liquids. With respect to liquid pharmaceutical compositions, solutions and suspensions are envisioned. Preferably, tolperisone is provided in a form suitable for oral administration.

For example, tablets can be made by compression or molding, optionally with one or more accessory ingredients or additives. Compressed tablets are prepared, for example, by compressing in a suitable tabletting machine, the active ingredients in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) and/or surface-active or dispersing agent.

Molded tablets are made, for example, by molding in a suitable tabletting machine, a mixture of powdered compounds moistened with an inert liquid diluent. The tablets may optionally be coated or scored, and may be formulated so as to provide slow or controlled release of the active ingredients, using, for example, hydroxypropylmethyl cellulose in varying proportions to provide the desired release profile. Tablets may optionally be provided with a coating, such as a thin film, sugar coating, or an enteric coating to provide release in parts of the gut other than the stomach. Processes, equipment, and toll manufacturers for tablet and capsule making are well-known in the art.

The compositions of the present invention may also be prepared in a form suitable for veterinary applications.

Administration

Methods of administering therapeutic formulations of tolperisone include but are not limited to oral, intra-arterial, intrathecal, intraspinal, intramuscular, intraperitoneal, intravenous, intranasal, and inhalation routes. Preferred routes of administration are intramuscular, intravenous, and oral. In a particularly preferred embodiment, tolperisone is administered orally. However, tolperisone may be administered by any suitable route, including without limitation, oral, rectal, nasal, topical (including transdermal, aerosol, buccal and sublingual), vaginal, parenteral (including subcutaneous, intramuscular, intravenous and intradermal), intrathecal, and pulmonary. The preferred route will, of course, vary with the condition and age of the recipient, the particular condition being treated, and the specific combination of drugs employed, if any.

Provided herein is a method of treating a subject with tolperisone under conditions that minimize exposure to 4-MMPPO. In certain embodiments, exposure to 4-MMPPO is minimized by administering a tolperisone composition of the invention containing 4-MMPPO in an amount of less than 10 ppm, and preferably, less than about 7 ppm. Such compositions can be prepared by any of the methods described herein. In preferred embodiments, the subject is treated with a tolperisone composition containing from about 10 ppm to about 1.5 ppm 4-MMPPO.

Treatment

Tolperisone is a centrally-acting muscle relaxant that acts on the central nervous system and is used mainly for the treatment of elevated muscle tone and tension, as well as for certain circulatory problems in the extremities. Tolperisone has been found to reduce experimental hypertonia and decerabration rigidity, as well as inhibit reticulospinal reflex facilitation without affecting cortical functions. It also improves peripheral blood flow (Toperin® Package Insert).

Tolperisone is useful in treating a number of conditions. For example, tolperisone may be administered to a subject suffering from one of more of the following conditions including: muscle spasm, spastic syndromes, muscle soreness, myotonia, dysmenorrhea, climacteric complaints, lockjaw, neurolatyrism, osteoarthritis or rheumatoid arthritis (when administered in combination with a non-steroidal anti-inflammatory drug), rheumatic diseases, fibromyalgia syndrome, occupational and sport-related stress, back pain, spasticity caused by neurological diseases, multiple sclerosis, myelopathy, encephalomyelitis, stroke, muscular hypertension, muscular contracture, spinal automatism, obliterative vascular diseases (e.g., obliterative arteriosclerosis, diabetic angiopathy, obliterative thromboangitis, Raynaud's disease, diffuse scleroderma), disorders due to injured innervation of the vessels (acrocyanosis, intermittent angioneurotic dysbasis), neuropathic pain, and in individual cases, post-thrombotic venous and lymphatic circulation disorders, diabetic neuropathy, post-herpetic neuralgia, and crural ulcer (Myolax® Package insert).

Subjects to whom tolperisone may be administered include both children (aged three months to 18 years), and adults (18 years and older).

Dosage

A therapeutic amount of tolperisone can be empirically determined and will vary with the particular condition being treated, the subject, and the like. The actual dose to be administered will vary depending upon the age, weight, and general condition of the subject as well as the severity of the condition being treated, the judgment of the health care professional, and particular dosage form being administered.

A therapeutically effective amount of tolperisone can be determined by those skilled in the art, and will be adjusted to the requirements of each particular case. Generally, a therapeutically effective amount of tolperisone for an adult will range from a total daily dosage of between about 10 and 3000 mg/day, preferably, in an amount between 25-2000 mg/day, more preferably, in an amount between about 50-1800 mg/day. Typical dosage ranges for adults include total daily dosage ranges from about 150-1000 mg/day, preferably from about 150 to about 750 mg/day, administered as either a single dosage or as multiple dosages. Preferred in certain embodiments are divided dosages over the course of a day, e.g., a recommended daily dose divided into five doses, or four doses, or three doses, or two doses. Preferred dosage amounts include dosages from about 50 mg to 450 mg twice daily or three times daily. That is to say, dosage amounts may be selected from 50 mg/day, 100 mg/day, 150 mg/day, 200 mg/day, 250 mg/day, 300 mg/day, 350 mg/day, 400 mg/day, 450 mg/day, 500 mg/day or more.

Depending upon the dosage amount and precise condition to be treated, administration can be one, two, or three times daily for a time course of one day to several days, weeks, months, and even years, and may even be for the life of the patient. Illustrative dosing regimes will last a period of at least about a day, a week, from about 1-4 weeks, from 1-3 months, from 1-6 months, from 1-50 weeks, from 1-12 months, or longer. Dosage amounts for children ranging in age from 3 months to 18 years in age range from about 1-25 mg/kg/day, preferably from about 2-15 mg/day, in from about 2-4 divided doses, preferably 3 doses. Exemplary recommended dosage ranges for children include 5-10 mg/kg/day and from 2-4 mg/kg/day, in 2-3 divided doses.

Practically speaking, a unit dose of any given composition of the invention or active agent can be administered in a variety of dosing schedules, depending on the judgment of the clinician, needs of the patient, and so forth. The specific dosing schedule will be known by those of ordinary skill in the art or can be determined experimentally using routine methods.

Additionally, the dosage of a tolperisone composition administered to a subject can be limited to prevent overexposure of the subject to 4-MMPPO. In a preferred embodiment, less than 45 μg of 4-MMPPO per dose of tolperisone is administered to the subject, and less than 135 μg of 4-MMPPO is administered to the subject per day. The duration of treatment of a subject with tolperisone can also be kept relatively short (2 weeks or less) in order to keep 4-MMPPO levels within tolerable limits for the subject.

EXAMPLES

The following examples illustrate certain aspects and advantages of the present invention, however, the present invention is in no way considered to be limited to the particular embodiments described below.

The practice of the invention will employ, unless otherwise indicated, techniques of pharmaceutical formulation, separations, pharmacology, and the like, which are within the skill of the art, based upon the guidance provided herein. See, for example, *Handbook of Pharmaceutical Manufacturing Formulations*, S. K. Niazi (ed.), CRC Press, 2004; Goodman & Gilman, *The Pharmacological Basis of Therapeutics*, 9th Edition, Hardman, J. G., Gilman, A. G., Limbird, L. E. (eds.), McGraw-Hill, New York, 1995; *Basic and Clinical Pharmacology*, 18th Edition, Katzung, B. G. (ed.), Appleton & Lange, Norwalk, Conn., 2001.

In the following examples, efforts have been made to ensure accuracy with respect to numbers used (e.g., amounts, temperatures, etc.) but some experimental error and deviation should be accounted for. Each of the following examples is considered to be instructive to one of ordinary skill in the art for carrying out one or more of the embodiments described herein.

Example 1

Analysis of Commercial Tolperisone Compositions for 4-MMPPO Content

Tolperisone compositions were obtained from various commercial sources and analyzed for 4-MMPPO content by HPLC-MS/MS.

All samples used in the analytical sequence were prepared for analysis as follows. Sample were homogenized if necessary (e.g., tablets) and weighed. For each tolperisone sample, approximately 20 mg of sample was added into a 20 mL flask. 20 mL of 50 mM HCl in MeOH was added to the flask, which was then placed in an ultrasonic bath for about 5 minutes. The contents of the flask were mixed on a vortexer for about 20 seconds. In instances in which the tolperisone sample had initially been in tablet form, the solution was then centrifuged at 4000 rpm for 2 minutes. 200 μL of the sample was then transferred into a small conical centrifuge vial. 20 μL of an internal standard solution containing deuterated 4-MMPPO, 200 μL of buffer at pH 1, and 0.4 mL of diisopropyl ether (DIPE) were added to the vial. The sample was then extracted by vortexing with a DVX-2500 multi-tube vortexer (2100 rpm) for about 2 minutes (cycle: 5 seconds run, 1 second pause time) and centrifugation (phase separation) at 4000 rpm for 2 minutes. 150 μL of 50 mM HCl in MeOH/DMSO (½) was added into empty designated conical autosampler vials. After centrifugation, 100 μL of supernatant was transferred into these conical autosampler vials. The vials were crimped and vortexed with a DVX-2500 multi-tube vortexer (2100 rpm) for about 1 minute. 7 μL of the prepared sample was then injected immediately into an HPLC-MS/MS system or the sample was stored at a temperature below −20° C. until analysis. The chromatography conditions and mass spectrometry parameters used for analysis of 4-MMPPO are shown below in Tables 1 and 2, respectively.

TABLE 1

CHROMATOGRAPHIC CONDITIONS FOR ANALYSIS OF 4-MMPPO

| | |
|---|---|
| Mobile phase solvent A | 50 mM formic acid in water |
| Mobile phase solvent B | 50 mM formic acid in MeOH |
| Gradient | 0.0 min: switching LC to waste, external (50% methanol) to MS |
| | 0.0-0.8 min linear: 45% B → 67% B |
| | 0.8-1.7 min linear: 67% B → 88% B (LC to MS) |
| | 1.7-2.4 min isocratic: 45% B (LC to waste) |
| Flow | 1 mL/min |
| Column | LUNA ® HPLC column (Phenomenex, Germany); C$_{18}$ bonded silica gel 5 μm, C18(2), 2 × 50 mm |
| Column temperature | 50° C. |
| Retention time | approximately 1.3 min: 4-MMPPO and D7-4-MMPPO |
| Injection volume | 7 μL |

TABLE 2

MS-DETECTION OF 4-MMPPO

| | |
|---|---|
| MS detection | Atmospheric pressure chemical ionization interface (APCI) in positive ion mode |
| Vaporizer temperature | 450° C. |
| Corona needle current | 5 μA |
| Gas 1 | pressure = 60 psi |
| Curtain gas | pressure = 45 psi |
| Lateral position | approximately 5 units (default) |
| Vertical position | approximately 10 units |
| Quadrupole resolution | unit → unit |
| Detection mode | MRM |
| Transitions | 161.1 → 143.1 m/z: 4-MMPPO |
| | 161.1 → 128.1 m/z: 4-MMPPO-qual |
| | 168.1 → 150.1 m/z: D7-4-MMPPO |
| | 168.1 → 132.1 m/z: D7-4-MMPPO |

TABLE 3

4-MMPPO CONTENT IN COMMERCIALLY AVAILABLE TOLPERISONE FORMULATIONS

| Sample No. | Manufacturer* | Lot No. | Dosage | Manuf. Date | Time from Manuf. Date to Analysis | [4-MMPPO], ppm |
|---|---|---|---|---|---|---|
| 1 | A | 204406 | 150 mg | August 2006 | 6 | 68 |
| 2 | A | 204506 | 150 mg | August 2006 | 6 | 56 |
| 3 | A | 206506 | 150 mg | August 2006 | 6 | 51 |
| 4 | A | 257506 | 100 mg | November 2006 | 3 | 40 |
| 5 | A | 167106 | 150 mg | June 2006 | 8 | 100 |
| 6 | B | 243806 | 150 mg | October 2006 | 4 | 15 |
| 7 | B | 247106 | 150 mg | September 2006 | 5 | 14 |
| 8 | B | 247206 | 150 mg | September 2006 | 5 | 19 |
| 9 | B | 307003 | 150 mg | July 2003 | 43 | 22 |
| 10 | C | T66612A | 50 mg | June 2006 | 8 | 215 |
| 11 | C | T6A207A | 150 mg | October 2006 | 4 | 107 |
| 12 | D | 506223 | 50 mg | May 2005 | 21 | 442 |

*A = Merck; B = Viatris (now part of Meda AB, Sweden); C = Mydeton ®, D = ; Mydocalm ®

As a result of the analytical 4-MMPPO assay developed by the inventors and its sensitivity to extremely low levels of detection, the data in the table above revealed significant amounts of 4-MMPPO in each sample examined, and certainly in excess of the levels contained in the purified tolperisone formulations described herein and in the examples which follow. Most notable are samples 1, 2, 3, 5 and 10, 11, 12, each of which contain surprisingly high levels of 4-MMPPO, i.e., greater than 50 ppm 4-MMPPO. Due to the association of 4-MMPPO with genotoxicity, the inventors recognized an immediate need to arrive at formulations of tolperisone having levels of 4-MMPPO that are significantly lower than current commercial formulations such as those above.

Upon recognizing this shortcoming with currently available formulations of tolperisone, the inventors explored and arrived at various approaches to providing pure compositions of tolperisone having levels of 4-MMPPO that are significantly reduced from those levels found in prior art formulations, such as those described above and also described in U.S. Patent Application No. 2006/0041141. The formulations provided herein possess the advantage of possessing 4-MMPPO-associated genotoxic side effects that are significantly reduced over the prior art formulations (such as those represented by the illustrative sampling above), by virtue of their lowered (i.e., minimal) levels of 4-MMPPO).

Example 2

Standard Recrystallization of Tolperisone

Tolperisone samples identified during production as containing 4-MMPPO at levels of greater than 0.5% by weight were employed as starting material (referred to as 'crude'). Crude tolperisone was dissolved in an 85:15 (v/v) mixture of 2-butanone (methyl ethyl ketone) and isopropanol under reflux for 30 minutes. The resulting solution was cooled to 80° C., and the solution was filtered while hot. The filtered solution was then cooled to 5° C., and stirred for an additional 7 hours. The resulting crystalline precipitate was separated by filtering, followed by washing with methyl ethyl ketone. The recrystallized material was dried in vacuo at 45-85° C.

Based upon HPLC-MS/MS analysis, the recrystallized tolperisone possessed 0.14% by weight 4-MMPPO; in subsequent production batches, 4-MMPPO was detected to be less than but around 0.05% (500 ppm), but nowhere near the desired level of 10 ppm or below. This may have been due to the amount of tolperisone contained in the starting material, such that the amount was greater than could be substantially removed in a single recrystallization, or due to the presence of residual methyl ethyl ketone in the recrystallized product, which upon heating to dry the product facilitated formation of 4-MMPPO, or a combination thereof.

The resultant recrystallized tolperisone possessed levels of 4-MMPPO which were considered unsatisfactory for administration to a subject, due to the potential for associated genotoxic side effects related to the level of 4-MMPPO.

Example 3

Multiple Stage Recrystallization of Tolperisone

The approach utilized in Example 2 above was repeated with the exception that multiple stage (repeated) recrystallizations were carried out.

TABLE 4

4-MMPPO Content Following Repeated Recrystallizations, Non-Acifidified Solvent

| Batch | [4-MMPPO], ppm Crude Tolperisone | [4-MMPPO], ppm After 1st Recryst. | [4-MMPPO], ppm After 2nd Recryst. | [4-MMPPO], ppm After 3rd Recryst. |
|---|---|---|---|---|
| 1 | 107/51.1 before/after drying | <6.6 | 8.3 | <6.6 |
| 2 | 7/<6.6 | 7.3 | 6.2 | — |

As can be seen from the results in Table 4, multiple recrystallizations from solvents/solvent systems such as methyl ethyl ketone and isopropanol can be effective to provide tolperisone that is substantially absent 4-MMPPO.

Example 4

Recrystallization of Tolperisone Followed by Acid Wash

Crude tolperisone having a 4-MMPPO content of greater than 0.05% by weight was dissolved in an 85:15 mixture of 2-butanone (MEK) and isopropanol under reflux for 12 hours. The temperature was decreased to 80° C. and the solution filtered while hot. The filtered solution was cooled to 5° C. and stirred for 7 h at 5° C.

The crystalline precipitate was separated by filtering and washed with a 1% HCl/isopropanol mixture, and subsequently dried in vacuo at 45 to 85° C.

Based upon the recognition of potential side reactions of tolperisone as demonstrated in FIGS. 1 and 2, the inventors realized the benefit of an absence of base in minimizing the occurrence of β-elimination of either tolperisone or its corresponding α-hydroxy ketone side product to form 4-MMPPO, and the value of recrystallization and/or washing the product in the presence of acid.

Based upon HPLC-MS/MS analysis, a content of 4-MMPPO in the range of 1.5 to 10 ppm was detected in the recrystallized product, revealing a surprising and significant improvement over currently available commercial formulations of tolperisone.

Example 5

Recrystallization of Tolperisone Using Acidified Solvent System

Crude tolperisone was dissolved in an 85:15 (v/v) mixture of 2-butanone (MEK) and isopropanol, accompanied by addition of 1% HCl under reflux for 12 hours. The temperature was decreased to 80° C. and the solution filtered while hot. The solution was cooled to 5° C. and stirred for 7 h at 5° C.

The crystalline precipitate was separated by filtering, washed with isopropanol, and subsequently dried in vacuo at 45 to 85° C., with lower drying temperatures being preferred.

Tolperisone showed enhanced stability during recrystallization in the presence of acid. When 1% (v/v) concentrated aqueous HCl was added to the recrystallization mixture, 4-MMPPO levels dropped below 6.6 ppm in the final recrystallized tolperisone product.

Example 6

Multiple Recrystallizations of Tolperisone Using Acidified Solvent System

Crude tolperisone (Lot SPH-3047, Batches 1 and 2) was dissolved in an 85:15 (v/v) mixture of 2-butanone (MEK) and isopropanol, accompanied by addition of 1% HCl, under reflux for 12 hours. The temperature was decreased to 80° C. and the solution filtered while hot. The solution was cooled to 5° C. and stirred for 7 h at 5° C.

The crystalline precipitate was separated by filtering, washed with isopropanol, and subsequently dried in vacuo at 45 to 85° C., with lower temperatures being preferred.

The above recrystallization process was repeated 4 times.

TABLE 5

4-MMPPO Content Following Repeated Recrystallizations Using Acidified Solvent

| Batch | [4-MMPPO], ppm Crude Tolperisone | [4-MMPPO], ppm After 1st Recryst. | [4-MMPPO], ppm After 2nd Recryst. | [4-MMPPO], ppm After 3rd Recryst. | [4-MMPPO], ppm After 3rd Recryst. |
|---|---|---|---|---|---|
| 1 | 107/51.1 Before/after drying | <6.6 | <6.6 | <6.6 | <6.6 |
| 2 | 7/<6.6 | <6.6 | <6.6 | <6.6 | <6.6 |

While the first recrystallization under acidified conditions exhibited the most significant removal of 4-MMPPO and purification of tolperisone, additional recrystallizations were also effective in further reducing the content of 4-MMPPO in the final drug product.

Example 7

Investigation of 4-MMPPO Levels in Tolperisone Drug Lots Versus Manufactured Tablets

TABLE 6

MS-DETECTION OF 4-MMPPO IN DRUG LOTS AND IN TABLETTED FORMULATIONS

| Lot No. Tablet | Manufacturer | Drug Lot in Tablet | [4-MMPPO in Drug Lot or API], ppm | Time from Manuf. Date to Analysis (mos) | [4-MMPPO in Tablet], ppm |
|---|---|---|---|---|---|
| 257506/040 | A | SFO192 | 21 | 3 | 39 |
| 204406 | A | SD0108, SE0107 | 14, 20 | 6 | 66 |
| 204506 | A | SF0093 | — | 6 | 56 |
| 206506 | A | SF0094 SF0096 | — | 6 | 51 |
| 167106 | A | SD0108 SE0107 | 14, 20 | 8 | 99 |
| 243806 | B | SF0191 SF0192 | 22, 21 | 4 | 14 |
| 247206 | B | SF0097 | — | 4 | 18 |
| 247106 | B | SF0095 | — | 5 | 13 |
| 307003 | B | SB0068 | 39 | 43 | 21 |

*A = Merck; B = Viatris (now part of Meda AB, Sweden);

Lots of tolperisone were obtained from manufacturers A and B, as were the final manufactured tablet formulations. Analyses were carried out as described in Example 1 to determine 4-MMPPO levels in both drug lots and final manufactured formulations. As can be seen from an examination of Table 5 above, in nearly 90% of the cases, a notable increase in the level of 4 MMPPO was observed when comparing drug lots (API, manufactured drug per se, i.e., absent additives, stabilizers, excipients, etc.) with final pharmaceutical formulations (in this case, tablets).

As a result of this study, the inventors recognized the problem of 4-MMPPO not only present in drug lots, but also in final pharmaceutical formulations. Based upon the results in the table above, it appears that 4-MMPPO is formed not only during preparation of tolperisone (API), and/or during its purification, and/or during formulation (e.g., blending), but also forms as a degradant during the shelf life (i.e., upon storage) of the final pharmaceutical formulation. Thus, based upon this data, the inventors further recognized the advantage of minimizing formation of 4-MMPPO not only during preparation of tolperisone, or in the purified drug product per se, but also in the final pharmaceutical formulation over its shelf life.

Example 8

Instant Release Caplet Formulation

A solution of anhydrous citric acid, 2-butanone and isopropyl alcohol is prepared. Tolperisone hydrochloride containing less than 10 ppm 4-MMPPO is transferred into a granulator, into which the already prepared solution is placed. This mixture is homogenized and subsequently dried in a drier at 60° C., or more preferably, at 40° C. The formed granulate is sifted through a 1.8 mm screen. Silicon dioxide and talcum are added and likewise mixed. Subsequently, the mixture is further mixed with magnesium stearate.

Tablets having a diameter of 8 mm and a weight of 155.8-172.2 g are produced. The finished granulate is coated with a suspension of hypromellose/hypromellose phthalate in ethanol/water, dyes and additives in a coating tank at a temperature of 55-60° C. The coated tablets are subsequently dried at room temperature.

Example 9

Controlled Release Formulation

Tolperisone containing less than 10 ppm 4-MMPPO as described herein is granulated as the hydrochloride salt in a mixer with a solution consisting of Eudragit RS in butanone with addition of anhydrous citric acid. Subsequently, Eudragit S and Eudragit L are incorporated homogeneously; the mixture is dried and sifted. To the sifted granulate are added tabletting auxiliary agents, and the granulate is tabletted. Tablets having a diameter of 8 mm and a weight of 190 mg are pressed.

Subsequently, the tablets are coated ("filmed") with a film material consisting of Eudragit L, dyes, and miscellaneous auxiliary agents, which are dissolved in butanol.

TABLE 7

| Ingredient | Grams |
|---|---|
| Tolperisone hydrochloride | 150.00 |
| Eudragit RS | 1.88 |
| Eudragit L | 14.24 |
| Eudragit S | 10.50 |
| Aerosil | 1.80 |
| Stearic acid | 1.80 |
| Glycerol dibehenate | 7.50 |
| Iron oxide dye | 0.08 |
| Titanium dioxide | 4.08 |
| Talcum | 6.03 |
| Polyethylene glycol | 1.02 |
| Dimethylpolysiloxane | 0.05 |

What is claimed is:

1. A method of relaxing a muscle in a subject, comprising:
   a. administering to a subject in need thereof a therapeutically effective amount of tolperisone, or a pharmaceutically acceptable salt or hydrate thereof, comprising 10 ppm 2-methyl-1-(4-methylphenyl)-propenone (4-MMPO) or less.

2. The method according to claim 1, wherein the tolperisone, or a pharmaceutically acceptable salt or hydrate thereof, comprises 9 ppm 4-MMPPO or less.

3. The method according to claim 1, wherein the tolperisone, or a pharmaceutically acceptable salt or hydrate thereof, comprises 8 ppm 4-MMPPO or less.

4. The method according to claim 1, wherein the tolperisone, or a pharmaceutically acceptable salt or hydrate thereof, comprises 7 ppm 4-MMPPO or less.

5. The method according to claim 1, wherein the pharmaceutically acceptable salt of tolperisone comprises tolperisone hydrochloride.

6. The method according to claim 1, wherein the tolperisone, or a pharmaceutically acceptable salt or hydrate thereof, is formulated as a pharmaceutical composition comprising one or more excipients.

7. The method according to claim 1, wherein the therapeutically effective amount of tolperisone, or a pharmaceutically acceptable salt or hydrate thereof, is between about 10 mg/day and 3,000 mg/day.

8. The method according to claim 1, wherein the therapeutically effective amount of tolperisone, or a pharmaceutically acceptable salt or hydrate thereof, is between about 150 mg/day and 1,000 mg/day.

9. The method according to claim 1, wherein administering occurs by an oral, intra-arterial, intrathecal, intraspinal, intramuscular, intraperitoneal, intravenous, intradermal, intranasal, inhalation, rectal, nasal, topical, transdermal, aerosol, buccal, sublingual, vaginal, parenteral, subcutaneous, pulmonary, or inhalation route of administration.

10. The method according to claim 1, wherein administering occurs by oral administration.

11. A method of treating muscle spasms or spasticity in a subject, comprising:
    a. administering to a subject in need thereof a therapeutically effective amount of a pharmaceutical composition comprising tolperisone hydrochloride, said pharmaceutical composition having less than 10 ppm 2-methyl-1-(4-methylphenyl)-propenone (4-MMPO).

12. The method according to claim 11, wherein the pharmaceutical composition has less than 9 ppm 4-MMPPO.

13. The method according to claim 11, wherein the pharmaceutical composition has less than 8 ppm 4-MMPPO.

14. The method according to claim 11, wherein the pharmaceutical composition has less than 7 ppm 4-MMPPO.

15. The method according to claim 11, wherein the therapeutically effective amount of said pharmaceutical composition is between about 10 mg/day and 3,000 mg/day.

16. The method according to claim 11, wherein said subject is treated for muscle spasms.

17. The method according to claim 11, wherein said subject is treated for spasticity.

18. The method according to claim 1, wherein the tolperisone, or a pharmaceutically acceptable salt or hydrate thereof, comprises 6 ppm 4-MMPPO or less.

19. The method according to claim 1, wherein the tolperisone, or a pharmaceutically acceptable salt or hydrate thereof, comprises 5 ppm 4-MMPPO or less.

20. The method according to claim 1, wherein the tolperisone, or a pharmaceutically acceptable salt or hydrate thereof, comprises 4 ppm 4-MMPPO or less.

21. The method according to claim 1, wherein the tolperisone, or a pharmaceutically acceptable salt or hydrate thereof, comprises 3 ppm 4-MMPPO or less.

22. The method according to claim 1, wherein the tolperisone, or a pharmaceutically acceptable salt or hydrate thereof, comprises 2 ppm 4-MMPPO or less.

23. The method according to claim 11, wherein the pharmaceutical composition has less than 6 ppm 4-MMPPO.

24. The method according to claim 11, wherein the pharmaceutical composition has less than 5 ppm 4-MMPPO.

25. The method according to claim 11, wherein the pharmaceutical composition has less than 4 ppm 4-MMPPO.

26. The method according to claim 11, wherein the pharmaceutical composition has less than 3 ppm 4-MMPPO.

27. The method according to claim 11, wherein the pharmaceutical composition has less than 2 ppm 4-MMPPO.

* * * * *

UNITED STATES PATENT AND TRADEMARK OFFICE
CERTIFICATE OF CORRECTION

PATENT NO. : 9,662,317 B2  
APPLICATION NO. : 15/068006  
DATED : May 30, 2017  
INVENTOR(S) : Gaeta et al.

Page 1 of 1

It is certified that error appears in the above-identified patent and that said Letters Patent is hereby corrected as shown below:

On the Title Page

At Item (72), Inventors:
At Lines 3 and 4, delete "Beate Katz" and insert --Beate Kaelz--

Signed and Sealed this
Twenty-third Day of July, 2019

Andrei Iancu
*Director of the United States Patent and Trademark Office*